(12) United States Patent
Dong et al.

(10) Patent No.: US 8,555,696 B2
(45) Date of Patent: Oct. 15, 2013

(54) METHODS OF CALIBRATING A FLUID ANALYZER FOR USE IN A WELLBORE

(75) Inventors: Chengli Dong, Sugar Land, TX (US); Ricardo R. Vasques, Bailly (FR); Michael O'Keefe, Tasmania (AU); Peter S. Hegeman, Stafford, TX (US); Oliver C. Mullins, Ridgefield, CT (US); Go Fujisawa, Kanagawa-Ken (JP); Stephane Vannuffelen, Meudon (FR); Richard Jackson, Lagos (NG); Ahmad Saputra, Jakarta (ID)

(73) Assignee: Schlumberger Technology Corporation, Sugar Land, TX (US)

( * ) Notice: Subject to any disclaimer, the term of this patent is extended or adjusted under 35 U.S.C. 154(b) by 171 days.

(21) Appl. No.: 12/666,309

(22) PCT Filed: Jul. 3, 2008

(86) PCT No.: PCT/US2008/069128
§ 371 (c)(1),
(2), (4) Date: Dec. 2, 2010

(87) PCT Pub. No.: WO2009/009409
PCT Pub. Date: Jan. 15, 2009

(65) Prior Publication Data
US 2011/0061439 A1      Mar. 17, 2011

Related U.S. Application Data

(60) Provisional application No. 60/948,723, filed on Jul. 10, 2007.

(51) Int. Cl.
*G01N 21/00* (2006.01)

(52) U.S. Cl.
USPC .......................................................... 73/1.02

(58) Field of Classification Search
None
See application file for complete search history.

(56) References Cited

U.S. PATENT DOCUMENTS

| | | | |
|---|---|---|---|
| 7,114,562 B2 | 10/2006 | Fisseler et al. | |
| 7,124,819 B2 | 10/2006 | Ciglenec et al. | |
| 7,654,130 B2 * | 2/2010 | Shah et al. | 73/23.42 |
| 2007/0079662 A1 | 4/2007 | Zazovsky et al. | |
| 2007/0079962 A1 | 4/2007 | Zazovsky et al. | |
| 2007/0143023 A1 | 6/2007 | Betancourt et al. | |
| 2008/0093078 A1 | 4/2008 | Vasques et al. | |
| 2008/0121017 A1 * | 5/2008 | Shah et al. | 73/23.42 |
| 2009/0050369 A1 * | 2/2009 | Pop et al. | 175/42 |

FOREIGN PATENT DOCUMENTS

| | | |
|---|---|---|
| GB | 2402476 | 12/2004 |
| WO | WO98/45575 | 10/1998 |
| WO | WO01/51898 | 7/2001 |

\* cited by examiner

*Primary Examiner* — Robert R Raevis
(74) *Attorney, Agent, or Firm* — John Vereb

(57) ABSTRACT

Methods of calibrating a fluid analyzer for use in a wellbore are described. An example method of generating calibration data for a fluid analyzer for use in a downhole tool involves lowering a downhole tool including a fluid analyzer to a location in a wellbore, measuring, via the fluid analyzer, a characteristic value of a calibration fluid or a vacuum while the fluid analyzer is at the location, obtaining an expected characteristic value for the calibration fluid or the vacuum at the location, and comparing the measured characteristic value to the expected characteristic value to generate a calibration value for the fluid.

32 Claims, 9 Drawing Sheets

METHODS OF CALIBRATING A FLUID ANALYZER FOR USE IN A WELLBORE

This application is a national stage entry of PCT/US08/69128, whose international filing date is Jul. 3, 2008, and PCT/US08/69128 claims priority on 60/948,723, filed Jul. 10, 2007.

FIELD OF THE DISCLOSURE

This disclosure relates generally to sampling and analyzing formation fluids and, more particularly, to methods of calibrating a fluid analyzer for use in a wellbore.

BACKGROUND

Downhole fluid composition analysis is often used to provide information in real time about the composition of subterranean formation or reservoir fluids. Such real-time information can be advantageously used to improve or optimize the effectiveness of formation testing tools during a sampling processes in a given well (e.g., downhole fluid composition analysis allows for reducing and/or optimizing the number of samples captured and brought back to the surface for further analysis). Some known downhole fluid analysis tools such as the Live Fluid Analyzer (LFA) and the Composition Fluid Analyzer (CFA), both of which are commercially available from Schlumberger Technology Corporation, can measure absorption spectra of formation fluids under downhole conditions. Each of these known fluid analyzers provides ten channels, each of which corresponds to a different wavelength, that correspond to a measured spectrum ranging from visible to near infrared wavelengths. The output of each of the channels represents an optical density (i.e., the logarithm of the ratio of incident light intensity to transmitted light intensity), where an optical density (OD) of zero corresponds to 100% light transmission and an OD of one corresponds to 10% light transmission. The combined optical density output of the channels provides spectral information that can be used to determine the water fraction and composition of formation fluids.

To ensure that a fluid analyzer provides reasonably accurate water fraction and composition information for formation fluids, the fluid analyzer is typically subjected to a calibration procedure that evaluates the baseline drift or error of the fluid analyzer channels at multiple temperatures. The calibration procedure is usually carried out at the surface (e.g., in a laboratory) and is performed at temperatures that may correspond generally to downhole tool temperatures. Additionally, the calibration procedure may involve the use of air, an oil having well-known optical characteristics, and/or water. However, the above-mentioned known calibration procedure may not correct for measurement errors resulting from differences between the conditions under which the calibration was performed (typically a limited number of temperature data points and/or a limited temperature range) and actual downhole conditions, or measurement errors related to fluid analyzer drift or inaccuracy resulting from non-repeatable temperature sensitivity (e.g., drift hysteresis for different temperature cycles) of the fluid analyzer channels.

SUMMARY

An example method of generating calibration data for a fluid analyzer for use in a downhole tool involves lowering a downhole tool including a fluid analyzer to a location in a wellbore, measuring, via the fluid analyzer, a characteristic value of a calibration fluid or a vacuum while the fluid analyzer is at the location, obtaining an expected characteristic value for the calibration fluid or the vacuum at the location, and comparing the measured characteristic value to the expected characteristic value to generate a calibration value for the fluid analyzer.

Another example method of calibrating a fluid analyzer for use in a downhole tool involves lowering a downhole tool, including a fluid analyzer, into a wellbore, measuring, via the fluid analyzer, a characteristic of a calibration fluid or a vacuum while the downhole tool is in the wellbore, and using the measured characteristic and an expected characteristic of the calibration fluid or the vacuum to calibrate the fluid analyzer.

Yet another method of generating calibration information for a fluid analyzer involves measuring a response of the fluid analyzer to a calibration fluid or a vacuum at a location in a wellbore, comparing the measured response of the fluid analyzer to an expected response to the calibration fluid or the vacuum, and generating calibration information based on the comparison of the measured response and the expected response.

DETAILED DESCRIPTION

Figure 1:
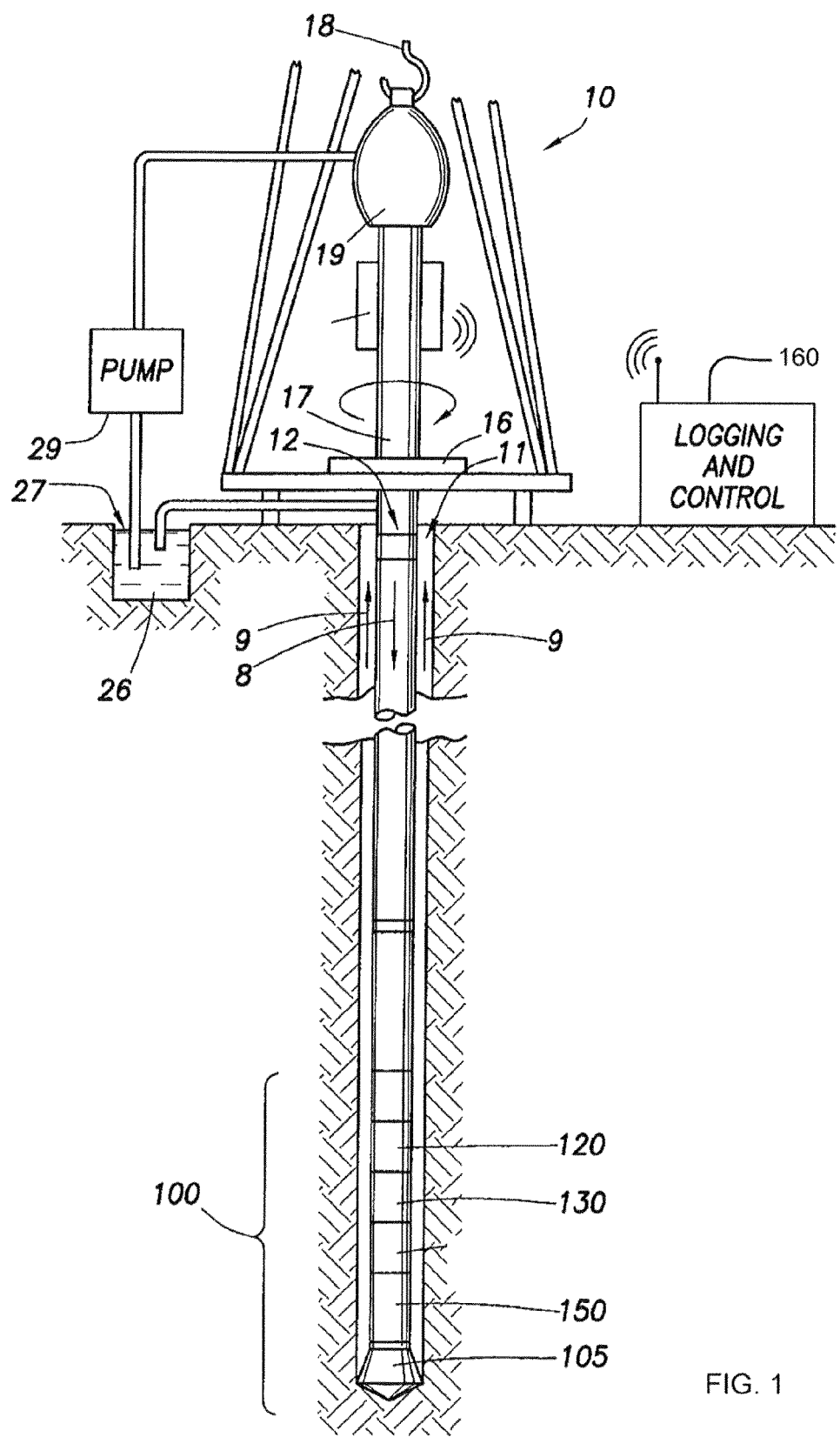
FIG. 1 depicts a wellsite system in which the example fluid analyzer calibration methods described herein can be employed.

Certain examples are shown in the above-identified figures and described in detail below. In describing these examples, like or identical reference numbers may be used to identify common or similar elements. The figures are not necessarily to scale and certain features and certain views of the figures may be shown exaggerated in scale or in schematic for clarity and/or conciseness.

Accurate analysis of formation fluid samples is a crucial aspect of efficiently producing a formation. In particular, the selection of a proper or best production methodology often depends on the results of a fluid analysis. As a result, proper calibration of downhole fluid analyzers is crucial to ensuring that fluid analysis results are accurate and, ultimately, that formation fluids are produced in the most effective and efficient manners.

Many known fluid analyzer calibration methods involve characterizing the response of a fluid analyzer to a known fluid (e.g., a J26 oil) at surface conditions (e.g., in a laboratory) and at one or more temperatures, which may or may not be similar to actual downhole temperature conditions. In contrast to these known methods, example fluid analyzer calibration methods described herein generate calibration data for a fluid analyzer by lowering a downhole tool, which includes the fluid analyzer and a stored quantity of calibration fluid, into a wellbore. The calibration fluid may be stored in one or more flowlines and/or a sample container of the downhole tool prior to lowering the downhole tool into the wellbore. Suitable calibration fluids include, but are not limited to, an alkane, an oil, water, air, nitrogen, carbon disulfide, and carbon dioxide. In some examples, the calibration fluid used may be substantially different in composition than a formation fluid to be measured by the fluid analyzer. For example, calibration fluids such as hydraulic oil, water, air, nitrogen, carbon disulfide, and carbon dioxide are substantially different in composition than many formation fluids to be measured by a fluid analyzer.

At one or more locations in the wellbore, the calibration fluid stored in the downhole tool is pumped into or otherwise disposed in or delivered to the fluid analyzer. The fluid analyzer then measures a characteristic value or values of the calibration fluid at the location. For example, the measured characteristic values may be spectral information obtained via one or more channels of the fluid analyzer and used to determine, for example, one or more optical density values at one or more wavelengths. The measured characteristic values of the calibration fluid are then compared to expected characteristic values of the calibration fluid at the location to generate calibration values for the fluid analyzer. The expected characteristic values may be based on measurements of the calibration fluid made at surface conditions (e.g., in a laboratory). In particular, to obtain the expected characteristic values, measurements of the calibration fluid made at surface conditions may be corrected for a change in its density at the location in the wellbore by using a density measurement at the location in the wellbore or an estimated density at the location. Each of the calibration values may correspond to a difference between an expected output of one of the fluid analyzer channels in response to the calibration fluid and the actual output of the channel in response to the calibration fluid at the location in the wellbore. Thus, the calibration values may be used to correct the measured outputs of each of the channels of the fluid analyzer (e.g., generate corrected characteristic values) at the location in wellbore.

The example calibration methods described in greater detail below may be performed at multiple locations in the wellbore while the downhole tool is stopped at a station or, if desired, while the tool is being run-in-hole (i.e., moving). Further, the example calibration methods may use a vacuum within the fluid analyzer instead of or in addition to a calibration fluid to generate calibration values for the fluid analyzer at one or more locations in a wellbore. A vacuum provides an optical density of zero for all of the fluid analyzer channels (e.g., wavelengths) at all temperatures and, thus, the expected characteristic values are all zero regardless of the location of the fluid analyzer in the wellbore.

The example fluid analyzer calibration methods described herein may be performed a location in a wellbore either prior to or after sampling a formation fluid at that location. As a result, the fluid analyzer is calibrated to compensate for actual downhole conditions (e.g., temperature, pressure, etc.) at the location as well as other non-ideal characteristics of the fluid analyzer (e.g., non-repeatability over temperature cycles, pressure cycles, etc.). By compensating for actual downhole conditions as well as other non-ideal characteristics of the fluid analyzer, the example calibration methods described herein provide a significantly more accurate calibration than the known calibration methods noted above because such known methods perform calibration under uphole or surface conditions, which are not necessarily similar or identical to downhole conditions and which do not compensate for other non-ideal characteristics of fluid analyzers such as, non-repeatability of the fluid analyzer over temperature cycles and the like.

While example methods are described herein with reference to so-called "sampling-while-drilling," "logging-while-drilling," and/or "measuring-while drilling" operations, the example methods may, additionally or alternatively, be used during wireline sampling operations. Moreover, such while-drilling operations do not require that sampling, logging and/or measuring actually occur while drilling is actively taking place. For example, as commonly performed in the industry, a drill bit of a drill string drills for a period of time, drilling is paused, one or more formation measurements and/or formation fluid samples are taken by one or more sampling, measuring and/or logging devices of the drill string, and then drilling is resumed. Such activities are referred to as sampling, measuring and/or logging while drilling operations because they do not require the removal of a drill string from the borehole in order to perform formation measurements and/or to obtain formation fluid samples.

FIG. 1 illustrates an example wellsite drilling system that can be employed onshore and/or offshore and which may employ the example fluid analyzer calibration methods described herein. In the example wellsite system of FIG. 1, a borehole 11 is formed in one or more subsurface formations by rotary and/or directional drilling.

As illustrated in FIG. 1, a drill string 12 is suspended within the borehole 11 and has a bottom hole assembly (BHA) 100 having a drill bit 105 at its lower end. A surface system includes a platform and derrick assembly 10 positioned over the borehole 11, the assembly 10 includes a rotary table 16, a kelly 17, a hook 18 and a rotary swivel 19. The drill string 12 is rotated by the rotary table 16, energized by means not shown, which engages the kelly 17 at the upper end of the drill string 12. The example drill string 12 is suspended from the hook 18, which is attached to a traveling block (not shown), and through the kelly 17 and the rotary swivel 19, which permits rotation of the drill string 12 relative to the hook 18. Additionally or alternatively, a top drive system could be used.

In the example of FIG. 1, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid 26 exits the drill string 12 via ports in the drill bit 105, and then circulates upwardly through the annulus region between the outside of the drill string and the wall of the borehole, as indicated by the directional arrows 9. The drilling fluid 26 lubricates the drill bit 105, carries formation cuttings up to the surface as it is returned to the pit 27 for recirculation, and creates a mudcake layer on the walls of the borehole 11.

The example BHA 100 of FIG. 1 includes, among other things, any number and/or type(s) of logging-while-drilling (LWD) modules (two of which are designated at reference numerals 120 and 120A) and/or measuring-while-drilling (MWD) modules (one of which is designated at reference numeral 130), a roto-steerable system and motor, and the example drill bit 105.

The example LWD modules 120 and 120A of FIG. 1 are each housed in a special type of drill collar as it is known in the art and each contain any number of logging tools and/or fluid sampling and analysis devices. The example LWD modules 120 and 120A include capabilities for measuring, processing, and/or storing information, as well as for communicating with surface equipment, such as a logging and control computer 160 via, for example, the MWD module 130.

An example manner of implementing a formation fluid sampling module for the LWD modules 120 and 120A, either or both of which may include a fluid analyzer to analyze formation fluid samples, is described below in connection with FIG. 3. Additionally, the example calibration methods described herein may be implemented by controlling the operations of the drill string 12, including the components of the BHA 100, via the logging and control computer 160. For example, the example calibration process of FIG. 10 may be implemented in conjunction with the logging and control computer 160 to control one or more of the LWD modules 120 and 120A and/or the MWD module 130 to measure spectral values (e.g., OD values) associated with a calibration fluid and/or a vacuum at one or more locations in the wellbore or borehole 11 and to use the measured values associated with the calibration fluid and/or vacuum to generate calibration values or information prior to or after sampling formation fluid (e.g., via one or more of the LWD modules 120 and 120A). In this manner, the calibration values or information can be used to calibrate the fluid analyzer(s), which may be used in one or more of the LWD modules 120 and 120A, under actual downhole conditions to eliminate calibration errors due to, for example, differences between surface calibration conditions and actual downhole conditions (e.g., temperatures, pressures, etc.) as well as other non-ideal characteristics of the fluid analyzer such as non-repeatability over temperature cycles, etc.

Other example manners of implementing an LWD module are described in U.S. Pat. No. 7,114,562, entitled "Apparatus and Method For Acquiring Information While Drilling," and issued on Oct. 3, 2006; and in U.S. Pat. No. 7,124,819, entitled "Downhole Fluid Pumping Apparatus and Method," and issued on Oct. 24, 2006. U.S. Pat. No. 7,114,562, and U.S. Pat. No. 7,124,819 are hereby incorporated by reference in their entireties.

The example MWD module 130 of FIG. 1 is also housed in a special type of drill collar and contains one or more devices for measuring characteristics of the drill string 12 and/or the drill bit 105. The example MWD tool 130 further includes an apparatus (not shown) for generating electrical power for use by the downhole system. Example devices to generate electrical power include, but are not limited to, a mud turbine generator powered by the flow of the drilling fluid, and a battery system. Example measuring devices include, but are not limited to, a weight-on-bit measuring device, a torque measuring device, a vibration measuring device, a shock measuring device, a stick slip measuring device, a direction measuring device, and an inclination measuring device.

Figure 2:
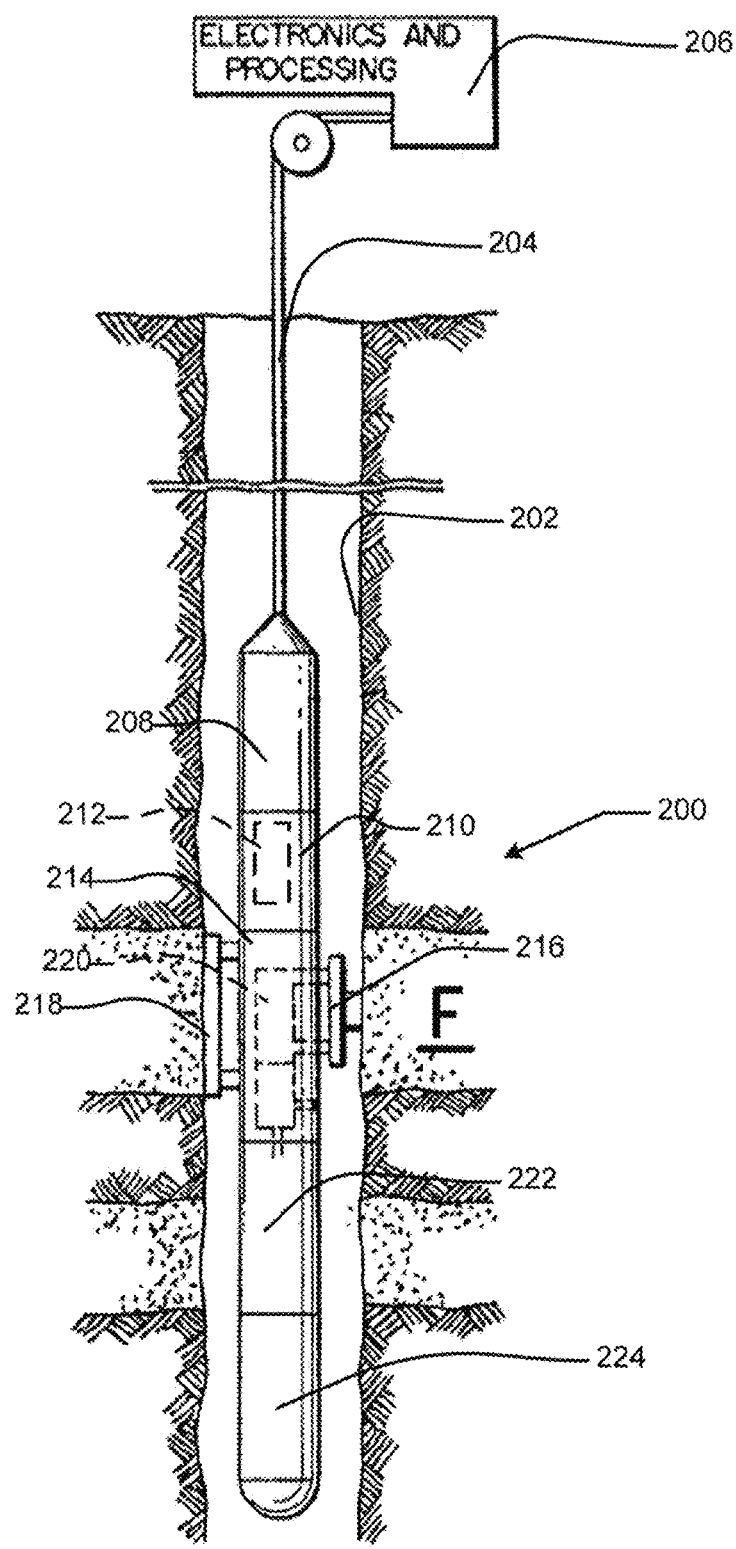
FIG. 2 depicts an example wireline tool that may be used to extract and analyze formation fluid samples in accordance with the example methods described herein.

Turning to FIG. 2, an example wireline tool 200 that may be used to extract and analyze formation fluid samples is suspended in a borehole or wellbore 202 from the lower end of a multiconductor cable 204 that is spooled on a winch (not shown) at the surface. At the surface, the cable 204 is communicatively coupled to an electrical control and data acquisition system 206. The tool 200 includes an elongated body 208 that includes a collar 210 having a tool control system 212 configured to control extraction of formation fluid from the formation F and measurements performed on the extracted fluid.

The wireline tool 200 also includes a formation tester 214 having a selectively extendable fluid admitting assembly 216 and a selectively extendable tool anchoring member 218 that are respectively arranged on opposite sides of the body 208. The fluid admitting assembly 216 is configured to selectively seal off or isolate selected portions of the wall of the wellbore 202 to fluidly couple the adjacent formation F and draw fluid samples from the formation F. The formation tester 214 also includes a fluid analysis module 220 through which the obtained fluid samples flow. The fluid may thereafter be expelled through a port (not shown) or it may be sent to one or more fluid collecting chambers 222 and 224, which may receive and retain the formation fluid for subsequent testing at the surface or a testing facility.

In the illustrated example, the electrical control and data acquisition system 206 and/or the downhole control system 212 are configured to control the fluid admitting assembly 216 to draw fluid samples from the formation F and to control the fluid analysis module 220 to measure the fluid samples. In some example implementations, the fluid analysis module 220 may be configured to analyze the measurement data of the fluid samples as described herein. In other example implementations, the fluid analysis module 220 may be configured to generate and store the measurement data and subsequently communicate the measurement data to the surface for subsequent analysis at the surface. Although the downhole control system 212 is shown as being implemented separate from the formation tester 214, in some example implementations, the downhole control system 212 may be implemented in the formation tester 214.

As with the drill string example shown in FIG. 1, the wireline tool 200 example of FIG. 2 may also be used in conjunction with the example fluid analyzer calibration methods described herein. For example, the formation tester 214 may be controlled by one or both of the downhole control system 212 and the electrical control and data acquisition system 206 to measure characteristic values of a calibration fluid and/or a vacuum at a location in the wellbore 202 and then compare the measured characteristic values to expected characteristic values to generate calibration information or values to be used to correct measurements of fluid from the formation F made by the formation tester 214. The calibration measurements made in accordance with the example fluid analyzer calibration methods described herein may be performed at one or more locations within the wellbore 202 and may be made while the wireline tool 200 is at a station (e.g., stationary and/or temporarily fixed in place at a location in the wellbore 202) and/or while the wireline tool 200 is being run-in-hole (i.e., moving within the wellbore 202).

Figure 3:
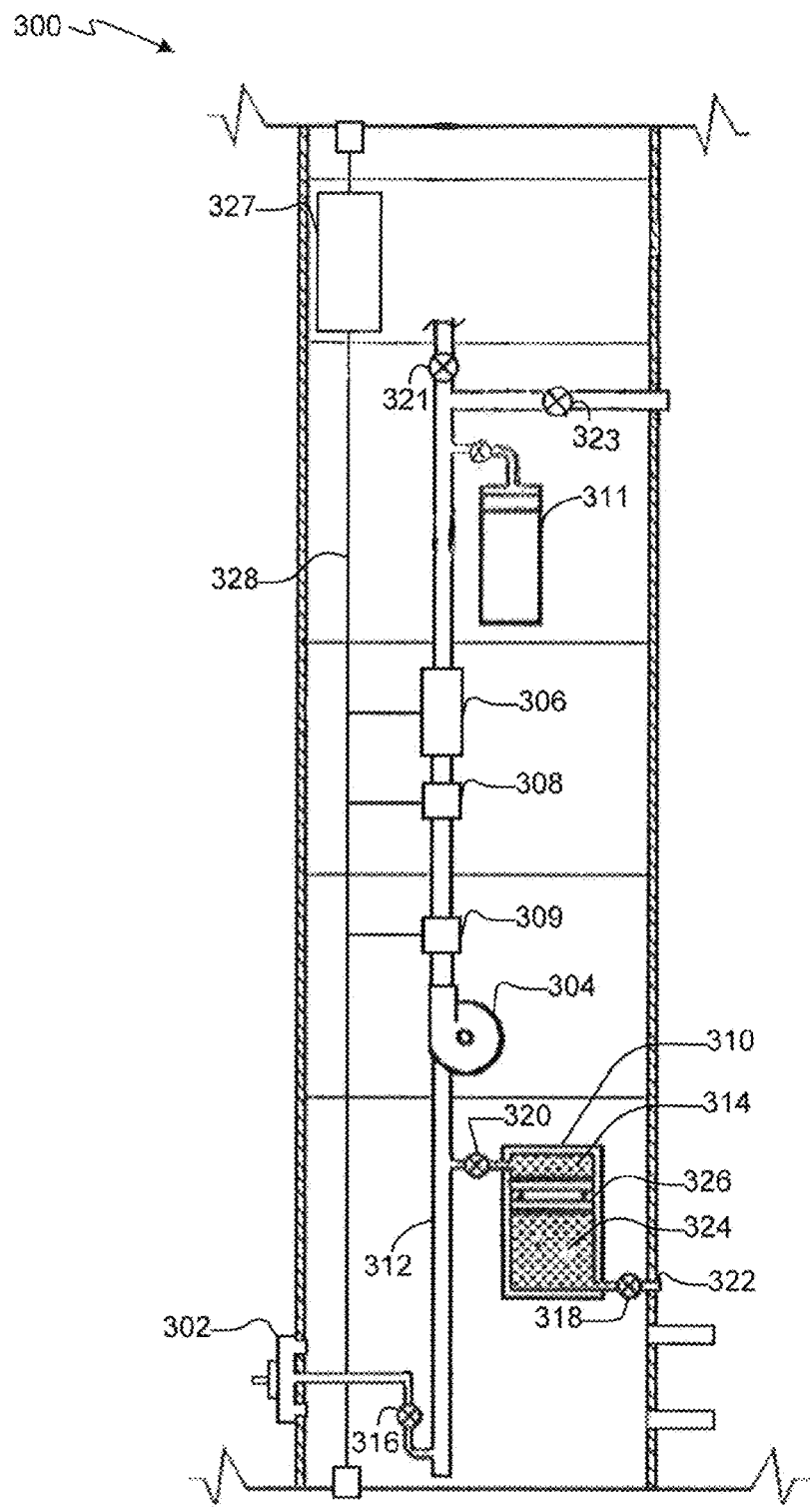
FIG. 3 depicts an example formation fluid sampling tool that may be used to implement the LWD tools of FIG. 1 and/or the wireline tool of FIG. 2.

FIG. 3 depicts an example formation sampling tool 300 that may be used to implement the formation tester 214 of FIG. 2 and/or the LWD modules 120 and 120A of FIG. 1. The example formation sampling tool 300 includes a probe assembly 302 to engage a surface of a wellbore to draw fluids from a formation. In other example implementations, straddle packers (not shown) can additionally or alternatively be used to engage and isolate a portion of the surface of the wellbore to draw fluids from a formation. The formation sampling tool 300 is provided with a pump 304 that may be used to draw fluids from a formation into the tool 300. The formation sampling tool 300 also includes one or more fluid sensors to measure the formation fluid drawn into the tool 300. More specifically, in the illustrated example, the formation sampling tool 300 is provided with a fluid analyzer 306 to measure one or more characteristics of formation fluid, calibration fluid and/or a vacuum as described in greater detail in connection with FIG. 10 below. The fluid analyzer 306 may be implemented using, for example, a light absorption/fluorescence spectrometer having a plurality of channels, each of which may correspond to a different wavelength. Thus, the fluid analyzer 306 may be used to measure spectral information for a calibration fluid, a vacuum, and/or a formation fluid. Such spectral information may include characteristic values such as optical density values associated with each of the channels. Of course, while the specific examples described herein relate to an optical fluid analyzer, the teachings of these examples may be more generally applied for use with other types of fluid analyzers including, for example, a fluid viscosity analyzer, a fluid resistivity analyzer, a nuclear magnetic resonance device, etc.

The tool 300 is also provided with one or more sensors 308 and 309 to measure pressure, temperature, density, viscosity, and/or any other fluid properties. The tool 300 may optionally include one or more fluid sample containers or stores 310 and 311, each including one or more fluid sample chambers in which reservoir fluid recovered during sampling operations can be stored and brought to the surface for further analysis and/or confirmation of downhole analyses. Alternatively or additionally, in accordance with the example fluid analyzer calibration methods described herein, the fluid sample container 310 and/or the container 311 may filled at the surface with a calibration fluid such as an alkane (e.g., n-heptane, n-octane, n-nonane, etc.), an oil (e.g., hydraulic oil such as J26 oil, synthetic oil, fuel oil such as diesel, oils with colorant such as diesel fuel with dye), water, nitrogen, air, carbon disulfide, carbon dioxide, or any other suitable calibration fluid. Alternatively or additionally, one or more portions of a flowline 312, which fluidly couples the fluid sample containers 310 and 311, the pump 304, the sensors 308 and 309, and the fluid analyzer 306 to the probe 302, may be filled at the surface with the calibration fluid.

Regardless of how the calibration fluid is stored in the tool 300 prior to being lowered into a wellbore, the example fluid analyzer calibration methods described herein control the various devices within the tool 300 to deliver at least some of the calibration fluid to the fluid analyzer 306. In one example, a volume of calibration fluid 314 may be stored in the sample container 310 while the tool 300 is at the surface. Then, when the tool 300 is lowered into a wellbore to a location at which a calibration of the fluid analyzer 306 is to be performed, a valve 316 is closed to block a fluid path between the probe 302 and the flowline 312, and valves 318 and 320 are opened. Opening the valve 318 enables wellbore fluid (e.g., drilling fluid), which is pressurized relative to the calibration fluid 314, to enter a port 322 and to begin to fill a chamber 324 that is separated from the calibration fluid 314 by a piston 326. As the volume of pressurized wellbore fluid 324 increases, the piston 326 is displaced upward to force at least some of the calibration fluid 314 through the valve 320 and into the flowline 312. The calibration fluid 314 may then flow via the flowline 312 into the fluid analyzer 306 to enable calibration of the fluid analyzer 306 in accordance with, for example, the method described below in connection with FIG. 10.

In another example, calibration fluid may be stored in the flowline 312 at the surface. After the flowline 312 is filled with the calibration fluid, the valves 316, 318, and 320 are closed. Then, the tool is located at the desired position in a wellbore and a calibration of the fluid analyzer 306 can be performed using the fluid stored in the flowline. In yet another example, calibration fluid may be stored in the sample container 311 at the surface and when a calibration of the fluid analyzer 306 is to be performed at a location in a wellbore, a valve 323 is closed and the pump 304 is operated in a reverse sampling direction to draw at least some of the calibration fluid from the container 311 into the fluid analyzer 306. In still another example, the flowline 312 and the fluid analyzer 306 may be evacuated to generate a vacuum therein and the valves 316, 320, 321, and 323 may be closed before the tool 300 is lowered into a wellbore. In that case, a calibration (under vacuum conditions) may then be performed at any time or depth. Of course, the foregoing methods of storing and delivering calibration fluid or a vacuum to the fluid analyzer 306 to perform a calibration of the fluid analyzer 306 at a wellbore location may be used separately or in any desired combination.

Figure 13:
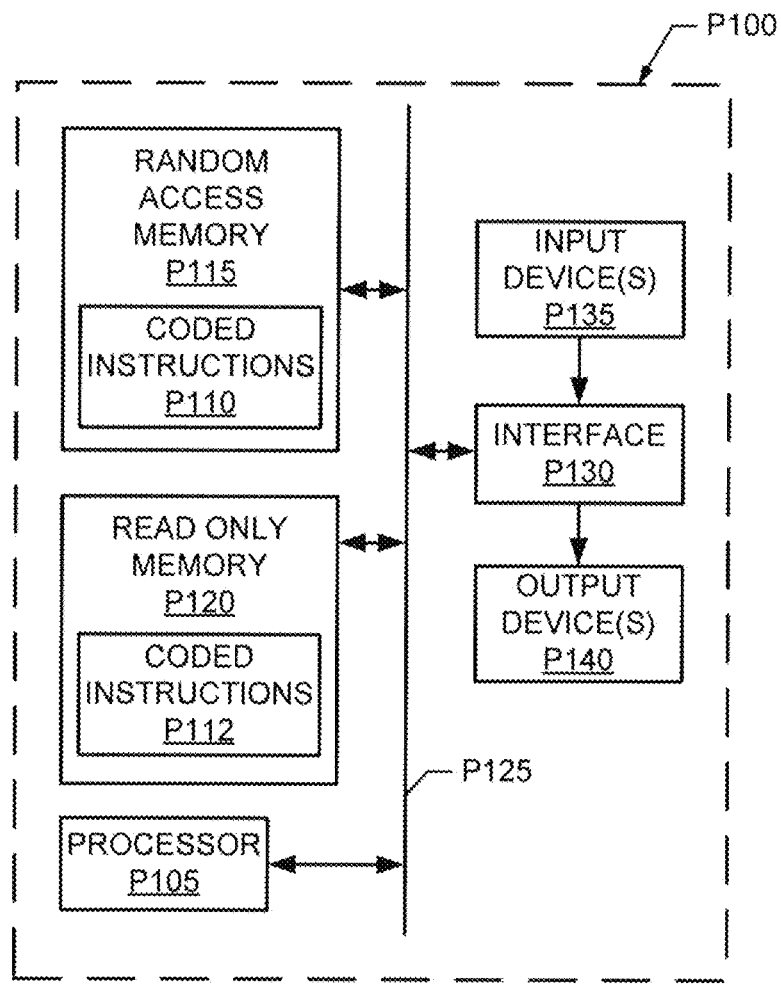
FIG. 13 is a schematic illustration of an example processor platform that may be used and/or programmed to implement any of all of the example methods and apparatus described herein.

To store, analyze and/or process test and measurement data (or any other data acquired by the formation sampling tool 300), the tool 300 is provided with a processing system 327, which may be generally implemented as shown in FIG. 13. In the illustrated example, the processing system 327 may includes a processor (e.g., a CPU and random access memory such as shown in FIG. 13) to control operations of the tool 300 and implement measurement routines (e.g., to control the fluid analyzer 306 to perform measurements of calibration fluid characteristics or a vacuum and to measure characteristics of formation fluid, etc.). To store machine readable instructions (e.g., code, software, etc.) that, when executed by the processing system 327, cause the processing system 327 to implement measurement processes or any other processes, the processing system 327 may be provided with an electronic programmable read only memory (EPROM) or any other type of memory (not shown). In the illustrated example, the processing system 327 is configured to receive digital data from one or more sensors (e.g., the fluid analyzer 306 and the sensors 308 and 309) provided in the tool 300.

Figure 10:
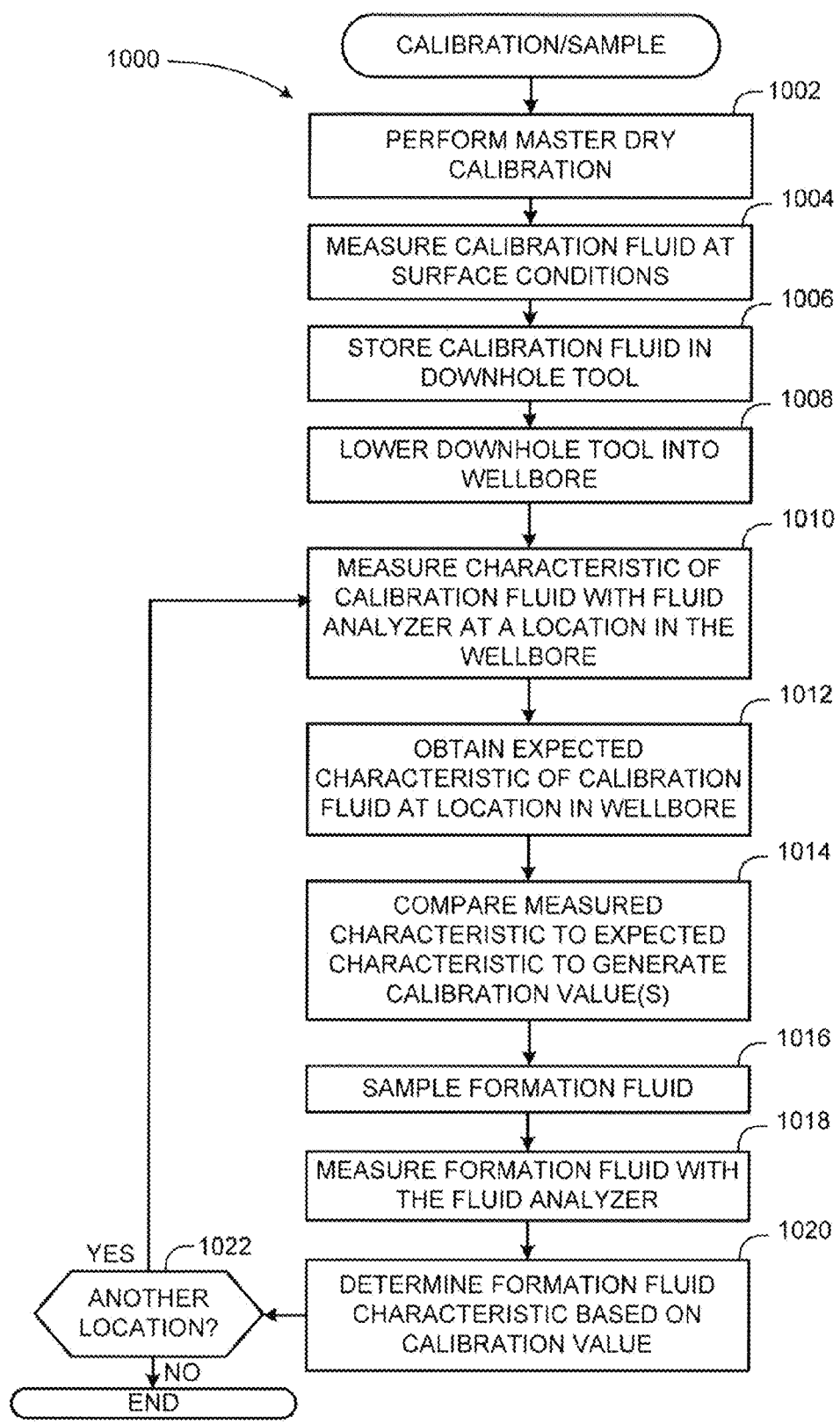
FIG. 10 is a flowchart of an example fluid analyzer calibration method.

To analyze measurement data such as spectral information associated with the calibration fluid or vacuum and/or formation fluid and obtained from the fluid analyzer 306, the processing system 327 is configured to calibrate the fluid analyzer 306 in accordance with the example calibration methods described herein (e.g., the example method of FIG. 10). In particular, the processing system 327 may calculate characteristic values (e.g., optical density values) from measurements made by the fluid analyzer 306 of a calibration fluid from the sample container 310, the sample container 311, and/or the flowline 312. The processing system 327 may also obtain expected characteristic values for the calibration fluid or the vacuum by retrieving expected characteristic information from a memory (e.g., one or both of the memories P115 and P120 of FIG. 13) and using the expected characteristic information in conjunction with actual downhole conditions, which may be measured by the sensors 308 and 309 or other sensors, to generate the expected characteristic values. For example, the processing system 327 may calculate or generate an expected optical density value for a calibration fluid based on a known optical density for the calibration fluid at surface pressure and use a density correction factor, which may be based on a density estimating equation or an actual downhole density measurement, to generate an expected optical density of the calibration fluid at the downhole location. The processing system 327 may then compare the measured characteristic values of the calibration fluid to the expected characteristic values to generate calibration values or information which, in turn, may be used by the processing system to correct measurements of formation fluid made by the fluid analyzer 306 as described in greater detail below. To communicate information when the tool 300 is downhole, the processing system 327 is communicatively coupled to a tool bus 328, which may be communicatively coupled to a surface system (e.g., the logging and control system 160, the electrical control and data acquisition system 206, etc.).

Additionally, the tool 300 may be configured to enable cleaning of the fluid analyzer 306 and/or the sensors 308 and 309 while downhole prior to performing a calibration to further improve the accuracy of the calibration. For instance, one or both of the sample containers 310 and 311 may contain a cleaning solution or fluid that may be injected into the flowline 312 to clean the fluid analyzer 306 and/or the sensors 308 and 309. In one example, a cleaning fluid may be stored in the container 311 and drawn through the fluid analyzer 306 and/or the sensors 308 and 309 via the pump 304. Alternatively or additionally, the sample chamber 310 may be initially filled with a cleaning fluid and injected into the flowline 312 to clean the fluid analyzer 306 and/or the sensors 308 and 309. Further details regarding cleaning of downhole components including flowlines, sensors, etc. may be found in U.S. Patent Publication No. 2008/0093078, which is incorporated by reference herein in its entirety.

Although the components of FIG. 3 are shown and described above as being communicatively coupled and arranged in a particular configuration, the components of the formation sampling tool 300 can be communicatively coupled and/or arranged differently than depicted in FIG. 3 without departing from the scope of the present disclosure. In addition, the example calibration methods described herein are not limited to a particular conveyance type but, instead, may be implemented in connection with different conveyance types including, for example, coiled tubing, wireline, wired-drill-pipe, and/or other conveyance means known in the industry.

Figure 4:
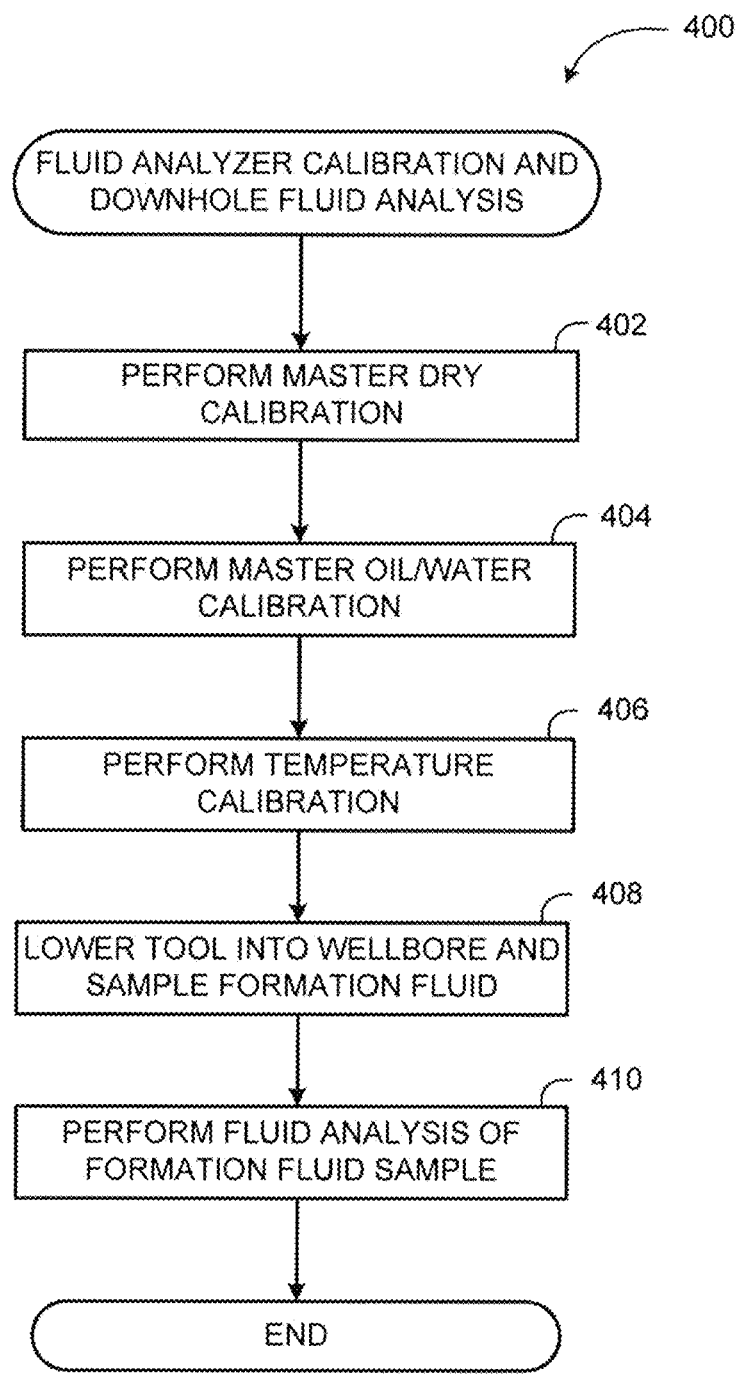
FIG. 4 is a flowchart depicting a known fluid analyzer calibration method.

To facilitate a better understanding of the operations and advantages of the example fluid analyzer calibration methods described herein, a brief discussion of a known fluid analyzer calibration method is first provided below in conjunction with FIGS. 4-7. FIG. 4 is a flowchart depicting a known method 400 to calibrate a fluid analyzer and to perform a downhole fluid analysis with the fluid analyzer following the calibration. In general, known fluid analyzer calibration methods such as the example method 400 primarily work to correct for baseline drift of fluid analyzer channels between about room temperature and an expected maximum temperature under which the fluid analyzer will be used in a downhole environment (e.g., a maximum tool temperature).

Figure 5:
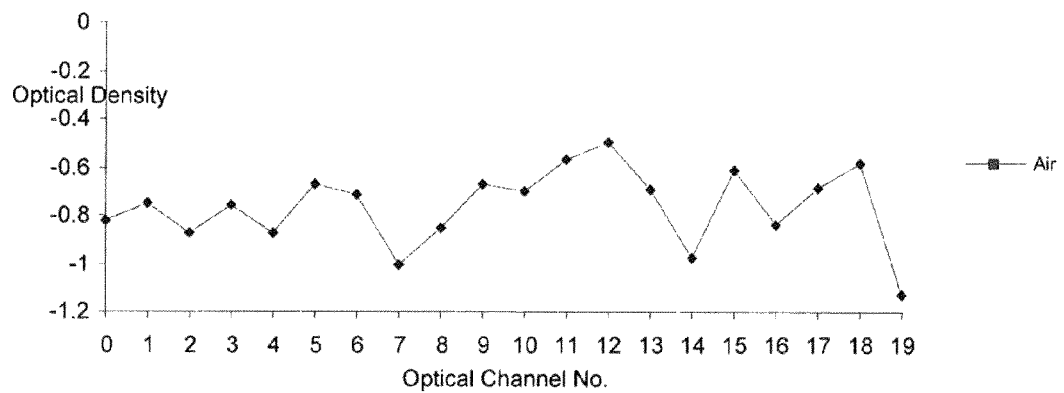
FIG. 5 is a graph depicting the baseline output of a fluid analyzer in response to air at room temperature.

Initially, a master dry calibration (block 402) is performed. The master dry calibration (block 402) is performed at room temperature with air in the fluid analyzer at atmospheric pressure. The master dry calibration (block 402) provides an optical density value for each channel of the fluid analyzer being calibrated. For example, FIG. 5 depicts a graph of optical density values for twenty channels of a known fluid analyzer. These optical density values, which vary significantly, may be stored and used to establish a baseline for each of the fluid analyzer channels for subsequent measurements of other fluids (e.g., formation fluids).

Figure 6:
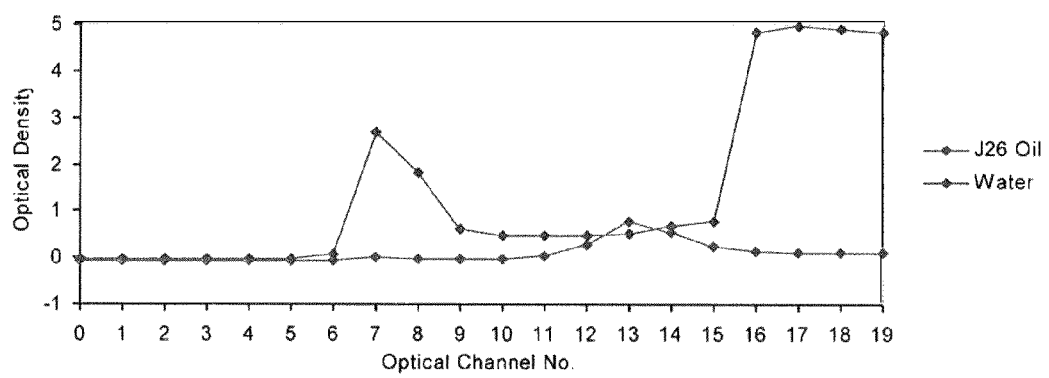
FIG. 6 is a graph depicting the output of the fluid analyzer associated with the graph of FIG. 5 in response to J26 oil and water.

Following the master dry calibration (block 402), the known calibration method 400 performs a master oil/water calibration (block 404). The master oil/water calibration (block 404) measures the response of the fluid analyzer to water and hydraulic oil (e.g., J26 type) separately at room temperature and low pressure (e.g., less than 100 pounds per square inch). FIG. 6 depicts a graph of optical density values for the same twenty channels of the known fluid analyzer associated with FIG. 5. The optical density values of FIG. 6 may be used to characterize the response of a fluid analyzer to water and hydraulic oil. In particular, the measured values may be compared to the expected values, and calibration data (e.g., similar to that shown in FIG. 5) may be generated therefrom.

Figure 7:
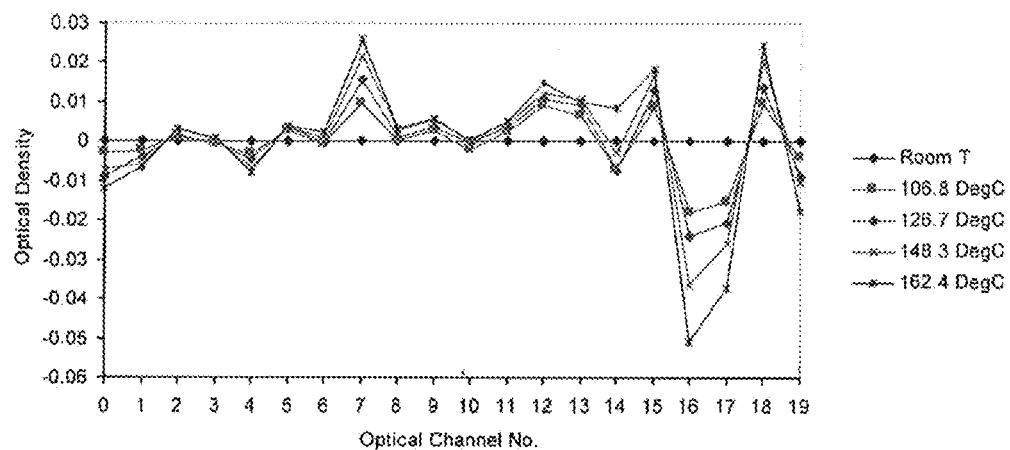
FIG. 7 is a graph depicting the output of the fluid analyzer associated with the graphs of FIGS. 5 and 6 in response to a range of ambient temperatures.

The known calibration method 400 then performs a temperature calibration process (block 406) during which the response of the fluid analyzer undergoing calibration to air is measured at atmospheric pressure for temperatures ranging from room temperature to a maximum expected operating environment temperature. Typically, a limited number of temperature points are selected ranging from about room temperature (e.g., 25° C.) to about 200° C., which represents a typical maximum operating temperature of a formation sampling tool. FIG. 7 depicts a graph of optical density values at different temperatures for the same twenty channels of the fluid analyzer associated with FIGS. 5 and 6 above. Thus, the optical density values shown in FIG. 7 may used to quantify the effect of temperature on the baseline outputs of each of the channels to enable correction of formation fluid measurements at various temperatures. In particular, the measured values may be compared to the expected values, and calibration data (e.g., similar to that shown in FIG. 5) may be generated therefrom to provide baseline values as a function of temperature.

Following the fluid analyzer calibration operations at blocks 402, 404 and 406, the formation sampling tool, including the calibrated fluid analyzer, is lowered into a wellbore and fluid is sampled from a formation at a location in the wellbore (block 408). The sampled fluid is then analyzed (block 410) to, for example, determine the optical densities of the formation fluid for each of the plurality of channels of the fluid analyzer. The raw outputs of the fluid analyzer are corrected using values obtained during one or more of the master dry calibration (block 404), the master oil/water calibration (block 406), and the temperature calibration (block 408).

Figure 8:
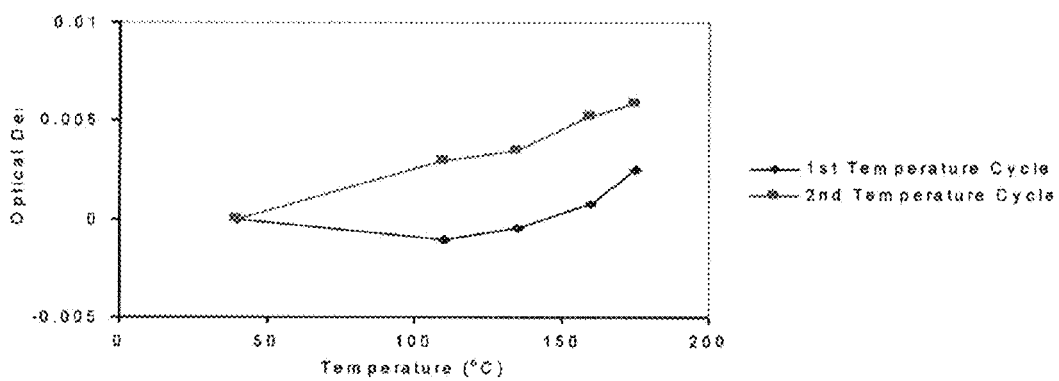
FIG. 8 is a graph depicting the output of the fluid analyzer associated with the graphs of FIGS. 5-7 in response to multiple temperature cycles.
Figure 9:
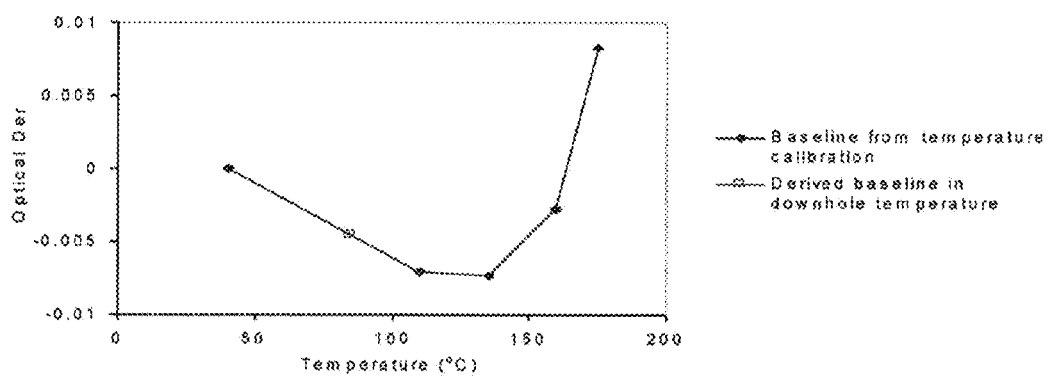
FIG. 9 is a graph depicting the output of one channel the fluid analyzer associated with the graphs of FIGS. 5-8 over a range of temperatures.

While the known calibration method 400 of FIG. 4 is useful to eliminate certain types of baseline errors that typically occur in fluid analyzers, this known method 400 does not correct for other common types of errors. For example, FIG. 8 is a graph depicting the non-repeatability of a fluid analyzer channel over different temperature cycles. Such non-repeatability errors cannot be corrected using a calibration method such as that shown in FIG. 4 because the variations from cycle to cycle are not accurately predictable. As another example, FIG. 9 is a graph depicting the baseline variation of a fluid analyzer channel over temperature, where the master calibrations with air, oil, and water have already been performed and used to arrive at the OD values shown in FIG. 9. In practice, the downhole temperatures experienced by a fluid analyzer may not match any of the temperature calibration points associated with the temperature calibration (e.g., block 406 of FIG. 4). As a result, many known fluid analyzer calibration methods use linear interpolation to derive baseline values between the temperature calibration points surrounding the actual downhole temperatures experienced by the fluid analyzer. However, such a process assumes that the temperature response of the fluid analyzer channel is linear or monotonic over temperature which, as can be easily seen in FIG. 9, is often not an accurate assumption. The foregoing types of calibration errors can have a significant negative effect on fluid sample measurements which, in turn, can have a significant negative effect on the accuracy of any formation fluid composition analysis performed using the inaccurate calibration data or information.

FIG. 10 is a flowchart depicting an example fluid analyzer process or method 1000 that may be used to calibrate a fluid analyzer under actual downhole conditions, thereby eliminating or substantially eliminating the effect of errors, such as those described above, which the known calibration techniques described herein have not been able to address. The example method 1000 may be implemented using machine readable instructions (e.g., software, code, etc.) executed by a processor, a controller and/or any other suitable processing device. For example, the method 1000 of FIG. 10 may be embodied in coded instructions stored on a tangible medium such as a flash memory, a read-only memory (ROM) and/or random-access memory (RAM) associated with a processor (e.g., the example processor P105 discussed below in connection with FIG. 13). Alternatively, the example method 1000 of FIG. 10 may be implemented using any combination(s) of circuit(s), ASIC(s), PLD(s), FPLD(s), discrete logic, hardware, firmware, etc. Also, the example method of FIG. 10 may be implemented manually or as any combination of any of the foregoing techniques such as, for example, any combination of firmware, software, discrete logic and/or hardware. Further, although the example operations of FIG. 10 have been described with reference to the flowchart of FIG. 10, many other methods of implementing the operations of FIG. 10 may be employed. For example, the order of execution of the blocks may be changed, and/or one or more of the blocks described may be changed, eliminated, sub-divided, or combined. Additionally, any or all the example operations of FIG. 10 may be carried out sequentially and/or carried out in parallel by, for example, separate processing threads, processors, devices, discrete logic, circuits, etc.

Turning in detail to FIG. 10, a master dry calibration (block 1002) is performed to obtain a baseline of all optical channels, each of which corresponds to a different wavelength, of the fluid analyzer being calibrated (e.g., the fluid analyzer 306 of FIG. 3). The master dry calibration (block 1002) is performed at surface conditions (e.g., room temperature and atmospheric pressure). The calibration fluid is then measured using the fluid analyzer to be calibrated at the surface conditions (block 1004). Typically, the surface conditions for the calibration fluid measurement at block 1004 are room temperature and a relatively low pressure such as less than 100 psig. Additionally, the calibration fluid may be J26 oil, or any other suitable fluid having proper absorptions in the visible to the near infrared range, or any other suitable range of wavelengths. Example calibration fluids include alkanes, hydraulic oils, synthetic oils, fuel oils, oils with colorants, water, nitrogen, air, carbon disulfide, and carbon dioxide. The calibration fluid used in the example method 1000 may be selected to suit the needs of a particular application or expected formation fluid sample type, downhole conditions, etc. More specifically, a particular calibration fluid may be selected to emphasize the calibration of certain optical channels or a particular range of optical channels corresponding to particular wavelengths or wavelength ranges. For example, alkanes and oils have main absorption peaks at wavelengths where most hydrocarbon absorptions occur. Oils with dye provide absorptions in the visible wavelength range and, thus, are well suited to characterize optical channels corresponding to the color absorption range of reservoir fluids. Nitrogen, air, and carbon disulfide have substantially no absorption in the visible and near infrared range and, thus, their absorption spectra are known and not related to their density and, as a result, these fluids are well suited to identify baseline drift and to calibrate fluid analyzer channels in the visible and near infrared range.

The calibration fluid is then stored in the downhole tool that will carry the fluid analyzer into the wellbore (block 1006). For example, the calibration fluid may be stored in the sample container 310, the sample container 311, and/or the flowline 312 of the formation sampling tool 300. The downhole tool, including the fluid analyzer, is then lowered into the wellbore (block 1008) in any desired manner. For example, the downhole tool may be a LWD tool such as shown in FIG. 1, a wireline tool such as shown in FIG. 2, or may be lowered using any other suitable conveyance including coiled tubing. The lowering operation (block 1008) may involve one or more station stops and/or may be a run-in-hole operation during which the lowering is substantially continuous.

Regardless of whether the lowering operation (block 1008) involves station stops or a run-in-hole operation, the fluid analyzer is used to measure a characteristic of the calibration fluid at a location in the wellbore (block 1010). The measurement operation (block 1010) involves disposing at least some of the stored calibration fluid in the fluid analyzer and measuring the absorption spectrum of the calibration fluid at the downhole conditions associated with the wellbore location. For example, in the case where the formation sampling tool 300 is used to perform the measurement operation (block 1010), calibration fluid stored in the flowline 312 and/or the sample container 311 may be delivered by the pump 304 to the fluid analyzer 306 when the tool 300 is at the wellbore location at which a calibration of the fluid analyzer 306 is to be performed. Alternatively, the calibration fluid may be delivered to the fluid analyzer 306 from the sample container 310 via a displacement of the piston 326 as described above in connection with FIG. 3. In the case where calibration fluid is only stored in the flowline 312, the calibration fluid substantially prevents drilling mud or other fluids or contaminants from entering the flowline 312 during the lowering of the downhole tool into the wellbore. However, the limited volume of fluid stored in the flowline 312 may limit the number of calibrations that can be performed. Further, once the sampling tool 300 has been used to sample a formation fluid, the flowline 312 will no longer contain any calibration fluid and, thus, calibration(s) following a formation sampling operation are not possible unless another source of calibration fluid is provided (e.g., the sample container 310). In the case where calibration fluid is alternatively or additionally stored in the sample container 310 and/or the sample container 311, calibrations can be performed at multiple locations or depths in the wellbore prior to and/or after formation sampling operations.

The measurement operation (block 1010) provides spectral information for the calibration fluid. In particular, the fluid analyzer (e.g., the fluid analyzer 306) outputs optical information or data associated with a plurality of channels, each of which corresponds to a different wavelength. The optical information may be optical density values or information or data associated with any other optical characteristic suitable for analyzing the composition of a fluid sample.

The example process or method 1000 then obtains the expected characteristic of the calibration fluid at the location (block 1012). For example, the expected optical density of the calibration fluid can be obtained by calculating an expected optical density for a particular wavelength or fluid analyzer channel using Beer-Lambert's law in accordance with Equation 1 below, where OD represents optical density values, $\lambda$ represents the wavelength associated with the fluid analyzer channel being calibrated, and $\rho$ represents density of the calibration fluid (at downhole and surface conditions).

$$OD_{expected,\lambda} = OD_{surface,\lambda} * \rho_{downhole} / \rho_{surface} \qquad \text{Equation 1}$$

The density of the calibration fluid at downhole conditions $\rho_{downhole}$ can be determined using a standard density estimating equation, which may use measurements of downhole temperature and pressure that are obtained via, for example, sensors in the downhole tool (e.g., the sensor 308 of FIG. 3). Alternatively, the density of the calibration fluid at downhole conditions can be measured directly via sensors in the downhole tool rather than calculated.

Alternatively, the expected optical density $OD_{expected,\lambda}$ can be determined via surface-based testing (e.g., in a laboratory) prior to lowering the downhole tool into the wellbore. During the surface-based testing, the calibration fluid may be measured with the fluid analyzer to be lowered with the downhole tool or a laboratory spectrometer at the same or substantially the same conditions to which the fluid analyzer will be exposed when at the one or more calibration locations downhole (i.e., in the wellbore). In cases where the actual downhole conditions are not known prior to lowering the downhole tool into the wellbore, the laboratory measurements (e.g., optical density values or spectral information) of the calibration fluid may include various temperatures and pressures providing ranges that extend over expected downhole conditions. During the downhole measurement operations, the optical densities of the calibration fluid measured in the laboratory can be used together with actual downhole temperatures and pressures to obtain (e.g., derive or calculate via interpolation) the expected characteristic (e.g., optical densities) at the location(s) in wellbore at which the fluid analyzer is being calibrated.

Figure 11:
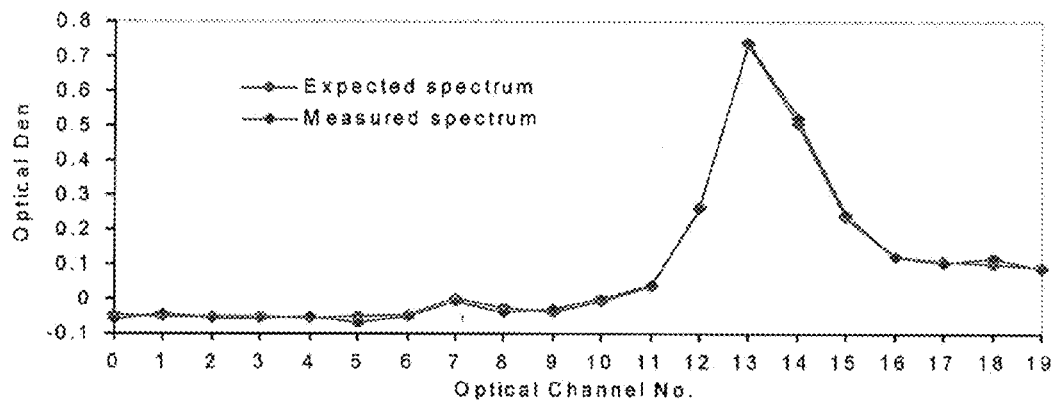
FIG. 11 is a graph depicting the expected and measured spectral information for twenty channels of a fluid analyzer being calibrated.
Figure 12:
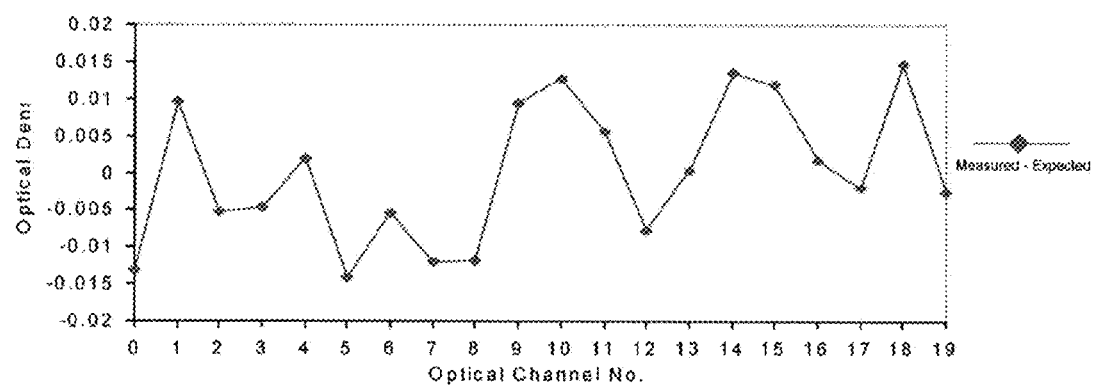
FIG. 12 is a graph depicting the difference between the measured and the expected spectral information shown in FIG. 11.

The measured characteristic obtained at block 1010 and the expected characteristic obtained at block 1012 are compared to generate a calibration value(s) (block 1014). More specifically, the difference between the measured spectral information associated with the response of the fluid analyzer to the calibration fluid (e.g., measured optical densities for each of the fluid analyzer channels in response to the calibration fluid) and the expected spectral information obtained at block 1012 is determined at block 1014. FIG. 11 is a graph depicting the measured and expected spectral information (e.g., optical density values in response to the calibration fluid) for twenty channels of the fluid analyzer. FIG. 12 is a graph depicting the difference between the measured and the expected spectral information. The differences can be used to generate calibration information or values for each of the fluid analyzer channels in accordance with Equation 2 below, where $OD_{C\_b,\lambda}$ is a corrected baseline calibration value for the fluid analyzer channel corresponding to wavelength $\lambda$ and downhole conditions, $OD_{baseline,\lambda}$ is the baseline OD of the same channel obtained during the master dry calibration at block 1002, and $OD_{measured,\lambda}$ is the OD of the same channel measured under downhole conditions at block 1010.

$$OD_{C\_b,\lambda} = OD_{baseline,\lambda} + OD_{expected,\lambda} - OD_{measured,\lambda} \qquad \text{Equation 2}$$

A formation fluid sampling operation (block 1016) may then be performed (e.g., the formation fluid sampling tool 300 and the fluid analyzer 306 may be used to measure the spectral information associated with the formation fluid sample (block 1018). For example, spectral information such as optical density values for the formation fluid sample across all channels of the fluid analyzer 306 may be obtained. The characteristic (e.g., optical density values) for the formation fluid sample may then be determined using the calibration values generated at block 1014 in accordance with Equation 2. Following determination of the formation fluid characteristic at block 1020, a determination of whether a calibration and/or sampling are to be performed at another location in the wellbore (block 1022) is performed. If another location calibration and/or sampling is to be performed, the process 1000 returns control to block 1010, otherwise the process 1000 ends.

While the example process or method 1000 depicts the sampling operations at blocks 1016, 1018 and 1020 as being performed at a wellbore location after the fluid analyzer has been calibrated at that location via the operations 1010, 1012 and 1014, the fluid analyzer could alternatively be calibrated via the operations 1010, 1012 and 1014 after a formation fluid sample is collected.

Some or all of the processing needed to perform the operations associated with the example process or method 1000 may be carried out using the processing system 327. For example, the computations associated with Equations 1 and 2 above may be performed by the processing system 327 or any other processing unit. Also, for example, in the case where expected characteristics (e.g., expected optical densities) are computed using laboratory data collected for the formation fluid for various temperatures and pressures, such data may be stored in a memory of the data processing system 327. Additionally or alternatively, some or all of the processing associated with the example process 1000 may be performed uphole using a surface processing device such as the logging and control system 160, the electrical control and data acquisition system 206, etc.

The example process or method 1000 can be modified or altered in several manners. For example, the fluid analyzer may be calibrated using a vacuum rather than a calibration fluid. In that case, a pump (e.g., the pump 304) may be used to generate a vacuum within a fluid analyzer (e.g., the fluid analyzer 306) and the response of the fluid analyzer (e.g., optical densities associated with each of the fluid analyzer channels) to the vacuum (e.g., at block 1010). To generate a vacuum in the fluid analyzer 306, for example, any fluid in the portion of the flowline 312 that fluidly couples the pump 304 to the sample container 311, is expelled into the wellbore by opening the valve 316, closing the valves 320, 321, and 323, and running the pump 304 in the reverse sampling direction to pull a vacuum in the fluid analyzer 306. After the vacuum is achieved, the valve 316 is closed and the pump 304 is stopped.

In the case where a vacuum is used, the expected optical densities for the channels are zero at all temperatures (e.g., at block 1012). The generation of calibration values for each of the channels is similar to that described above in connection with block 1014. In any event, a vacuum can be used to identify baseline drift for the purpose of calibrating the fluid analyzer for visible and near infrared wavelengths. Additionally or alternatively, the example process 1000 can be modified to eliminate the master dry calibration (block 1002) and only downhole calibration of the fluid analyzer is performed.

Still further, different types of calibration data may be combined to generate additional and/or different OD correction or calibration data. For example, calibration data associated with a master dry calibration (e.g., as shown in FIG. 5) and calibrations performed using water, oil, or any other fluid(s) (e.g., as shown in FIG. 6) may be combined to determine sensitivity information (as a function of wavelength) over temperature and/or pressure for a fluid analyzer (e.g., the fluid analyzer 306). Such sensitivity information could be used in addition to the baseline calibration data to further improve the accuracy of the calibration of a fluid analyzer. More generally, various types of calibration information (e.g., baseline, sensitivity, etc.) may be combined to provide transform functions (e.g., affine, multi-linear, etc.) for each channel or wavelength associated with a fluid analyzer.

FIG. 13 is a schematic diagram of an example processor platform P100 that may be used and/or programmed to implement all or a portion of any or all of the example operations of FIG. 10. For example, the processor platform P100 can be implemented by one or more general purpose processors, processor cores, microcontrollers, etc. The example processor platform P100, or a platform similar thereto, may be used to implement the logging and control system 160, the electrical control and data acquisition system 206, and/or the processing system 327.

The processor platform P100 of the example of FIG. 13 includes at least one general purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example process of FIG. 10 and/or to implement the example methods and apparatus described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown).

The processor platform P100 also includes an interface circuit P130. The interface circuit P130 may be implemented by any type of interface standard, such as an external memory interface, serial port, general purpose input/output, etc. One or more input devices P135 and one or more output devices P140 are connected to the interface circuit P130.

The example fluid analyzer calibration methods described herein enable a fluid analyzer to be calibrated under actual downhole conditions at wellbore locations associated with locations at which formation fluid is to be sampled and measured. As a result, the example calibration methods provide a remarkable improvement in the accuracy of fluid analyzer calibration by reducing or eliminating errors due to deriving baseline calibration values from relatively few calibration temperature points. For example, errors due to an inaccurate assumption that the temperature sensitivity of the fluid analyzer channels is a monotonic or linear function of temperature can be substantially reduced or eliminated using the example calibration methods described herein. Also, for example, calibration errors due to the non-repeatability of a fluid analyzer baseline across temperature cycles can be substantially reduced or eliminated, thereby further contributing to a remarkable improvement in the accuracy with which the composition of a formation fluid can be determined. A more accurate formation fluid composition determination can result in significant improvement in the efficiency with which formation fluid is produced from the formation as the well as the quality of the fluid extracted.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A method of generating calibration data for a fluid analyzer for use in a downhole tool, comprising:
lowering a downhole tool including a fluid analyzer to a location in a wellbore;
measuring, via the fluid analyzer, a characteristic value of a calibration fluid while the fluid analyzer is at the location;
obtaining an expected characteristic value for the calibration fluid at the location; and
comparing the measured characteristic value to the expected characteristic value to generate a calibration value for the fluid analyzer.

2. The method as defined in claim 1, wherein the calibration fluid is substantially different in composition than a formation fluid to be measured by fluid analyzer.

3. The method as defined in claim 1, wherein measuring the characteristic value of the calibration fluid comprises measuring spectral information.

4. The method as defined in claim 1, wherein the measured characteristic value and the expected characteristic value are optical density values.

5. The method as defined in claim 1, further comprising sampling a formation fluid while the fluid analyzer is at the location and using the calibration value prior to sampling the formation fluid or after sampling the formation fluid to generate a corrected characteristic value for the formation fluid.

6. The method as defined in claim 1, wherein the calibration fluid is at least one of an alkane, an oil, water, air, nitrogen, carbon disulfide, or carbon dioxide.

7. The method as defined in claim 1, wherein measuring the characteristic value of the calibration fluid comprises measuring optical density values at a plurality of wavelengths.

8. The method as defined in claim 1, further comprising obtaining the calibration fluid from a flowline of the downhole tool or a sample container of the downhole tool.

9. The method as defined in claim 8, further comprising disposing the calibration fluid in the flowline or the sample container prior to lowering the downhole tool into the wellbore.

10. The method as defined in claim 1, wherein obtaining the expected characteristic value comprises multiplying a first value corresponding to a characteristic of the calibration fluid at surface conditions by a second value representing a change in the density of the calibration fluid at the location relative to the surface conditions.

11. The method as defined in claim 10, wherein the first value is an optical density value.

12. The method as defined in claim 10, wherein the second value is a ratio of a value representing the density of the calibration fluid at the location and a value representing the density of the calibration fluid at the surface conditions.

13. The method as defined in claim 12, wherein the value representing the density of the calibration fluid at the location is obtained using a density estimating equation or a density measurement made by the downhole tool at the location.

14. The method as defined in claim 1, wherein obtaining the expected characteristic value comprises using conditions at the location to derive the expected characteristic value from a measurement of the calibration fluid made at the surface.

15. The method as defined in claim 14, wherein the measurement of the calibration fluid made at the surface comprises measuring an optical characteristic of the calibration fluid at the surface.

16. The method as defined in claim 14, wherein the measurement of the calibration fluid made at the surface is performed at expected downhole conditions.

17. The method as defined in claim 16, wherein the expected downhole conditions comprise a pressure and a temperature associated with the location.

18. The method as defined in claim 1, further comprising performing a baseline calibration of the fluid analyzer at the surface prior to lowering the downhole tool into the wellbore.

19. The method as defined in claim 18, wherein the baseline calibration comprises measuring a response of the fluid analyzer to air at surface conditions.

20. The method as defined in claim 1, wherein comparing the measured characteristic value to the expected characteristic value to generate the calibration value comprises determining a difference between the measured characteristic value and the expected characteristic value.

21. The method as defined in claim 1, wherein measuring the characteristic value of the calibration fluid or the vacuum comprises measuring a viscosity, measuring a resistivity, or performing a nuclear magnetic resonance measurement.

22. A method of calibrating a fluid analyzer for use in a downhole tool, comprising:
   lowering a downhole tool, including a fluid analyzer, into a wellbore;
   measuring, via the fluid analyzer, a characteristic of a calibration fluid while the downhole tool is in the wellbore; and
   using the measured characteristic and an expected characteristic of the calibration fluid to calibrate the fluid analyzer wherein measuring the characteristic of the calibration fluid comprises measuring a spectral characteristic of the calibration fluid.

23. The method as defined in claim 22, wherein the spectral characteristic comprises optical density values at a plurality of wavelengths.

24. A method of calibrating a fluid analyzer for use in a downhole tool, comprising:
   lowering a downhole tool, including a fluid analyzer, into a wellbore;
   measuring, via the fluid analyzer, a characteristic of a calibration fluid while the downhole tool is in the wellbore; and
   using the measured characteristic and an expected characteristic of the calibration fluid to calibrate the fluid analyzer wherein using the measured characteristic and the expected to calibrate the fluid analyzer comprises comparing the expected characteristic to the measured characteristic and using the result of the comparison to calibrate the fluid analyzer.

25. The method as defined in claim 24, wherein the expected characteristic is based on a known response of the calibration fluid to downhole conditions.

26. The method as defined in claim 24, wherein using the result of the comparison to calibrate the fluid analyzer comprises adjusting a baseline value of the fluid analyzer based on a difference between the expected characteristic and the measured characteristic.

27. A method of generating calibration information for a fluid analyzer, comprising:
   measuring a response of the fluid analyzer to a calibration fluid at a location in a wellbore;
   comparing the measured response of the fluid analyzer to an expected response to the calibration fluid; and
   generating calibration information based on the comparison of the measured response and the expected response.

28. The method as defined in claim 27, repeating the measuring, comparing and generating operations for multiple locations in the wellbore.

29. The method as defined in claim 27, further comprising obtaining the calibration fluid from a storage location within a downhole tool associated with the fluid analyzer.

30. The method as defined in claim 27, wherein comparing the measured response and the expected response comprises comparing spectral data.

31. A method of generating calibration data for a fluid analyzer for use in a downhole tool, comprising:
   lowering a downhole tool including a fluid analyzer to a location in a wellbore;
   measuring, via the fluid analyzer, a characteristic value of a vacuum while the fluid analyzer is at the location;
   obtaining an expected characteristic value for the vacuum at the location; and
   comparing the measured characteristic value to the expected characteristic value to generate a calibration value for the fluid analyzer.

32. A method of generating calibration information for a fluid analyzer, comprising:
   measuring a response of the fluid analyzer to a vacuum at a location in a wellbore;
   comparing the measured response of the fluid analyzer to an expected response to the vacuum; and
   generating calibration information based on the comparison of the measured response and the expected response.

* * * * *